United States Patent [19]
Korach et al.

[11] Patent Number: 5,650,550
[45] Date of Patent: Jul. 22, 1997

[54] MUTANT MICE HAVING A DEFICIT OF FUNCTIONAL ESTROGEN RECEPTORS

[75] Inventors: Kenneth S. Korach, Chapel Hill; Dennis B. Lubahn; Oliver Smithies, both of Durham, all of N.C.

[73] Assignee: The United States of America as represented by the Department of Health and Human Services, Washington, D.C.

[21] Appl. No.: 480,854

[22] Filed: Jun. 7, 1995

Related U.S. Application Data

[63] Continuation of Ser. No. 134,132, Oct. 1, 1993, abandoned.
[51] Int. Cl.$^6$ .............................. C12N 5/00; C12N 15/00
[52] U.S. Cl. .................. 800/2; 800/DIG. 1; 435/172.3; 435/354; 935/10; 935/70
[58] Field of Search .................... 800/2, DIG. 1; 435/172.3, 240.2, 320.1; 536/23.5, 23.1; 935/10,22, 70

[56] References Cited

U.S. PATENT DOCUMENTS 4,736,866  4/1988  Leder et al. ............................ 800/2

FOREIGN PATENT DOCUMENTS

WO9101140  2/1971  WIPO .

OTHER PUBLICATIONS

Arriza, J.L., et al. (1987) Cloning of human mineralocorticoid receptor complementary DNA: structural and functional kinship with the glucocorticoid receptor. Science 237:268–275.

Baker, A.R., et al. (1988) Cloning and expression of full-length cDNA encoding human vitamin D receptor. Proc. Natl. Acad. Sci. USA 85:3294–3298.

Boer, P.H., et al. (1990) Polymorphisms in the coding and noncoding regions of murine Pgk-1 alleles. Biochemical Genetics 28:299–307.

Chang, C., et al. (1988) Molecular cloning of human and rat complementary DNA encoding androgen receptors. Science 240:324–326.

Conneely, O.M., et al. (1986) Molecular cloning of the chicken progesterone receptor. Science 233:767–770.

Danielsen, M., et al. (1986) The mouse glucocorticoid receptor: mapping of functional domains by cloning, sequencing and expression of wild-type and mutant receptor proteins. EMBO J. 5:2513–2522.

Dickman, Z., et al. (1977) Does "blastocyst estrogen" initiate implantation? Science 195:687–688.

Dietz, H.C., et al. (1993) The skipping of constitutive exons in vivo induced by nonsense mutations. Science 259:680–683.

Eriksen, E.F., et al. (1988) Evidence of estrogen receptors in normal human osteoblast–like cells. Science 241:84–86.

Gambrell, R.D. (1992) Update on hormone replacement therapy. American Family Physician 46:87S–96S.

Gaspar, M.L., et al. (1991) A single–base deletion in the Tfm androgen receptor gene creates a short–lived messenger RNA that directs internal translation initiation. Proc. Natl. Acad. Sci. USA 88:8606–8610.

George, F.W. and Wilson, J.D. (1978) Estrogen formation in the early rabbit embryo. Science 199:200–202.

(List continued on next page.)

Primary Examiner—Bruce R. Campbell
Attorney, Agent, or Firm—Knobbe, Martens, Olson & Bear

[57] ABSTRACT

The present invention provides a mutant non-human vertebrate, in which all or some of the germ and somatic cells contain a mutation in at least one steroid hormone receptor allele, which mutation is introduced into the vertebrate, or an ancestor of the vertebrate, at an embryonic stage, and which mutation produces a phenotype in the vertebrate characterized by a deficit of functional steroid hormone receptors encoded by the allele. Also disclosed are related methods and constructs.

15 Claims, 1 Drawing Sheet

OTHER PUBLICATIONS

Gibson, M.K., et al. (1991) The mechanism of ICI 164,384 antiestrogenicity involves rapid loss of estrogen receptor in uterine tissue. Endocrinology 129:2000–2010.

Giguere, V., et al. (1987) Identification of a receptor for the morphogen retinoic acid. Nature 330:624–629.

Gorski, R. (1993) Editorial: Estradiol acts via the estrogen receptor in the sexual differentiation of the rat brain, but what does this complex do? Endocrinology 133:431–432.

Green, S., et al. (1986) Human oestrogen receptor cDNA: sequence, expression and homology to v–erb–A. Nature 320:134–139.

Harlap, S. (1992) The benefits and risks of hormone replacement therapy: An epidemiologic overview. Am. J. Obstet. Gynecol. 166:1986–1992.

Hollenberg, S.M., et al. (1985) Primary structure and expression of a functional human glucocorticoid receptor cDNA. Nature 318:635–641.

Hooper, M., et al. (1987) HPRT–deficient (Lesch–Hyhan) mouse embryos derived from germline colonization by cultured cells. Nature 326:292–295.

Horowitz, M.C. (1993) Cytokines and estrogen in bone: anti–osteoporotic effects. Science 260:626–627.

Jeltsch, J.M., et al. (1986) Cloning of the chicken progesterone receptor. Proc. Natl. Acad. Sci. USA 83:5424–5428.

Kim, H–S., et al. (1988) Recombinant fragment assay for gene targetting based on the polymerase chain reaction. Nucleic Acids Res. 16:8887–8903.

Koike, S., et al. (1987) Molecular cloning and characterization of rat estrogen receptor cDNA. Nucleic Acids Res. 15:2499–2513.

Koller, B.H. and Smithies, O. (1992) Altering genes in animals by gene targeting. Annu. Rev. Immunol. 10:705–730.

Koller, B.H., et al. (1991) Toward an animal model of cystic fibrosis: targeted interruption of exon 10 of the cystic fibrosis transmembrane regulator gene in embryonic stem cells. Proc. Natl. Acad. Sci. USA 88:10730–10734.

Korach, K.S. (1979) Estrogen action in the mouse uterus: characterization of the cytosol and nuclear receptor systems. Endocrinology 104:1324–1332.

Krust, A., et al. (1986) The chicken oestrogen receptor sequence: homolgy with v–erbA and the human oestrogen and glucocorticoid receptors. EMBO J 5:891–897.

Loosfelt, H., et al. (1986) Cloning and sequence analysis of rabbit progesterone–receptor complementary DNA. Proc. Natl. Acad. Sci. USA 83:9045–9049.

Lubahn, D.B., et al. (1988) Cloning of human androgen receptor complementary DNA and localization to the X chromosome. Science 240:327–330.

Luetteke, N.C., et al. (1993) TGFα deficiency results in hair follicle and eye abnormalities in targeted and waved–1 mice. Cell 73:263–278.

Mansour, S.L., et al. (1988) Disruption of the proto–oncogene int–2 in mouse embryo–derived stem cells:a general strategy for targeting mutations to non–selectable genes. Nature 336:348–352.

Mansour, S.L. (1990) Gene targeting in murine embryonic stem cells: introduction of specific alterations into the mammalian genome. GATA 7:219–227.

Misrahi, M., et al. (1987) Complete amino acid sequence of the human progesterone receptor deduced from clone cDNA. Biochem. Res. Commun. 143:740–748.

Pakdel, F., et al. (1990) Full–length sequence and in vitro expression of rainbow trout estrogen receptor cDNA. Mol. Cell. Endocrinol. 71:195–204.

Patel, P.D., et al. (1989) Molecular cloning of a mineralocorticoid (Type I) receptor complementary DNA from rat hippocampus. Molecular Endocrinology 3:1877–1885.

Pensler, J.M., et al. (1990) Osteoclasts isolated from membranous bone in children exhibit nuclear estrogen and progesterone receptors. J. Bone Mineral Res. 5:797–802.

Petkovich, M., et al. (1987) A human retinoic acid receptor which belongs to the family of nuclear receptors. Nature 330:444–450.

Ponglikitmongkol, M., et al. (1988) Genomic organization of the human oestrogen receptor gene. EMBO J 7:3385–3388.

Rhodes, D.; Klug, A. (1993) Zinc fingers. Scientific American. pp. 56–65 (Feb. 1993).

Robertson, M. (1987) Towards a biochemistry of morphogenesis. Nature 330:420–421.

Sluyser, M., et al. (1988) Assignment of estradiol receptor gene to mouse chromosome 10. J. Steroid Biochem. 31:757–761.

Weinberger, C., et al. (1986) The c–erb–A gene encodes a thyroid hormone receptor. Nature 324:641–646.

Whitcroft, S.I.J. and Stevenson, J.C. (1992) Hormone replacement therapy: risks and benefits. Clinical Endocrinology 36:15–20.

White, R., et al. (1987) Structural organization and expression of the mouse estrogen receptor. Molecular Endocrinology 1:735–744.

MUTANT MICE HAVING A DEFICIT OF FUNCTIONAL ESTROGEN RECEPTORS

This application is a File Wrapper Continuation of U.S. patent application Ser. No. 08/134,132, filed Oct. 1, 1993, abandoned.

FIELD OF THE INVENTION

The present invention relates to mutant non-human vertebrates having a deficit of functional steroid hormone receptors and related methods and constructs.

BACKGROUND OF THE INVENTION

Recent studies involving cloning and characterization of genes coding for various steroid hormone, thyroid hormone, vitamin D and retinoic acid receptors have indicated that these genes belong to a large family with similar structural and functional properties. Green et al., *Nature* 320: 134–139 (1986) (human estrogen receptor); Arriza et al., *Science* 237: 268–275 (1987) (human mineralocorticoid receptor); Hollenberg et al., *Nature* 318: 635–641 (1985) (human glucocorticoid receptor); Chang et al., *Science* 240: 324–326 (1988); (human androgen receptor); Lubahn et al., *Science* 240: 327–330 (1988) (human androgen receptor); Misrahi et al., *Biochem. Biophys. Res. Commun.* 143: 740–748 (1987) (human progesterone receptor); Weinberger et al., *Nature* 324: 641–646 (1986) (human thyroid hormone receptor); Baker et al., *Proc. Natl Acad. Sci. USA* 85: 3294–3298 (1988) (human vitamin D receptor); Giguere et al., *Nature* 330: 624–629 (1987) (human retinoic acid receptor); Petkovich et al., *Nature* 330: 444–450 (1987) (human retinoic acid receptor); Robertson, M., *Nature* 330: 420–421 (1987) (human retinoic acid receptor).

Steroid hormone, thyroid hormone and vitamin D and retinoic acid receptors constitute a class of regulatable transcription factors known as nuclear hormone receptors. Such factors bind high affinity to steroid, hormone or vitamin ligands that enter into target cells. *The Hormonal Control of Gene Transcription*, Cohen, P. and Foulkes, J. G., editors (Elsevier 1991). Once activated by steroids, hormones or vitamins, these receptors bind to DNA elements, termed "steroid response elements" (SREs), and stimulate initiation of transcription from target promoters.

The amino acid sequence characterizing the nuclear hormone receptor family can be divided into six regions: A–F. Two of these regions, C and E, form domains of known function. C constitutes the DNA-binding domain, and E the ligand-binding domain. Region C has a sequence motif characteristic of DNA-binding zinc fingers.

The DNA-binding domain of asteroid receptor is composed of approximately 80 amino acids that can be divided into two zinc finger units. Rhodes, D. and Klug, A. *Scientific American* pp56–65 (February 1993). The first zinc finger motif is thought to recognize specific base sequences in the cognate DNA. The second zinc finger motif is believed to function in dimerization of one receptor molecule with another receptor molecule.

Dimerization is required for steroid receptors to interact with DNA. Such receptors bind to DNA as pairs, because each protein in a pair recognizes half of a two-part target site that constitutes a palindrome. That is, each half of a response element is bound by one molecule in a receptor dimer. To bind successfully, the receptor must be able to distinguish both the specific base sequence of the half site and the spacing, i.e., the number of base pairs per half site.

The parts of the three-dimensional structure of the DNA-binding domain responsible for recognizing DNA and pairing with another receptor molecule have been elucidated. Each of the two zinc finger units consists of two parts: an irregular loop followed by an alpha helix. Each irregular loop is formed by the combining of four amino acids (e.g., cysteines) with a single zinc ion. The two fingers merge into a single arrangement where the two helices form a cross due to the mutual attraction of hydrophobic amino acids.

The amino acids that are critical for recognizing specific bases fall on the helix in the first unit. One alpha helix from each DNA binding domain thus makes contact with the bases of a DNA double helix. The function of the second helix is probably to serve as a backing strut to hold the recognition helix in place. Those amino acids that are responsible for forming a dimer reside in the irregular loop of the second unit. The pairing of the receptors through the dimerization region is thought to orient the dimer. That is, the two recognition helices on the dimer are arranged by dimerization so that the spacing between them matches the spacing defining the half site in the appropriate SRE.

Genomic cloning of human estrogen receptor sequences indicates that this gene is about 140 kb in length and is divided into eight exons. The N-terminal A/B region of the receptor is almost entirely encoded within the first exon. The DNA binding domain, region C, is encoded by exons 2 and 3. Exon 2 codes for the first zinc finger of the DNA binding domain, and exon 3 the second zinc finger. The "hinge" region, which is region D, is assembled by exon 4. The hormone binding domain, region E, is encoded in five exons, exons 4–8. The end of exon 8 encodes region F. These conclusions are based on the genomic organization of estrogen receptor genes from human (Ponglikitmongkol et al., *EMBO J* 7: 3385–3388 (1988)) but can be extended to other species and steroid hormone receptors.

The hallmark of steroid hormone receptors is their capacity to bind steroid hormonal ligands. There are five families of steroid hormones that can be classified on a structural and functional basis. Norman, A. W. and Litwack G., *Hormones* (Academic Press 1987). They are the estrogens (such as estradiol), the androgens (such as testosterone), the progestins (such as progesterone), the mineralocorticoids (such as aldosterone), and the glucocorticoids (such as cortisol). All of these steroid hormones are biologically derived from cholesterol.

The sex hormones of vertebrates, steroids derived from cholesterol in the gonads and adrenal cortex of both sexes, include the estrogens, the androgens, and the progestins. The estrogens and androgens are important in various aspects of growth and morphological differentiation, as well as in the development and regulation of sexual and reproductive behavior and cycles. Goodman, H. M., *Basic Medical Endocrinology* (Raven Press 1988). Estrogens predominate in the female, and androgens in the male. The production and secretion of these steroids is under the control of the gonadotropins, follicle stimulating hormone (FSH) and luteinizing hormone (LH), which are synthesized and secreted in the pituitary. These gonadotropins are, in turn, regulated by gonadotropin releasing hormone (GnRH), which is produced and released in the hypothalamus.

The estrogens are a family of steroids produced in the vertebrate ovary, testis, and adrenal cortex. Cholesterol is converted to progesterone, which is then transformed to the androgens, androstenedione and testosterone. The estrogens, of which estradiol-17β is the most potent, are made from these androgens.

The importance of estrogen in development and sexual differentiation is unresolved. Prenatal sexual differentiation has been shown to be dependent upon the secretion or absence of androgens during a critical period in development. Without androgens, the female configuration develops with the Mullerian ducts retained and the Wolffian ducts eliminated. In the presence of androgens, the male tract develops. By comparison, a role for estrogen during embryogenesis has been merely postulated. Estrogen synthesis is reported to be activated in male and female embryos at the time of blastocyst implantation in the uterus (George, F. W. and Wilson, J. D., *Science* 199: 200–202 (1978); Dickman et al., *Science* 195: 687–688 (1977)). A recent study, using a very sensitive reverse transcriptase-polymerase chain reaction technique, has detected estrogen receptor mRNA in blastocyst and 2-cell stage embryos (Hou, Q. and Gorski, J., *Proc. Nat. Acad. Sci. USA* (in press-MS#V1316)). Although estrogen is known to act via the estrogen receptor to mediate the sexual differentiation of the brain, its mode of action is not understood. (Gorski, R., *Endocrinology* 133: 431 (1993)).

A chemical interplay among estrogen, the gonadotropins, and GnRH occurs that is most apparent in the mammalian female and that begins, in humans, at menarche and continues until menopause. Norman, A. W. and Litwack G., *Hormones* (Academic Press 1987). It is known as the female reproductive cycle. Cyclical changes in FSH, LH, progesterone, estradiol, and GnRH are accompanied by morphological changes of the uterine endometrium. The cycle can be conveniently divided into two phases: pre- and postovulatory. The key events of the preovulatory phase are growth and maturation of the ovarian follicle and maturation of the uterine endometrium. The key event of the postovulatory phase is the growth, development, and involution of the corpus luteum and, in the absence of initiation of pregnancy, the shedding of the uterine endometrium. A 28-day cycle is generally regarded as the mean length of a normal menstrual cycle.

Throughout the menstrual cycle there is a changing ratio of FSH to LH. At the beginning of the follicular phase, from days 1 to 10, FSH blood levels exceed LH levels. At approximately day 10 there is a crossover, and LH rapidly becomes elevated to a very large peak or surge on the day of ovulation, day 14. Blood levels of FSH are increased at ovulation, but not to the extent achieved by LH. Throughout the luteal phase the levels of FSH are low, while LH levels are relatively high on days 14–18. LH levels fall to low levels in the absence of fertilization by day 28.

The secretions of FSH and LH are both believed to be governed by the same hypothalamic releasing factor, GnRH. This makes it difficult to devise biochemical mechanisms that can explain the changing ratio of FSH to LH throughout the menstrual cycle. One suggestion is that the response of the adenohypophysis cell which secretes FSH and LH in response to the hypothalamic-derived GnRH is determined by blood concentrations of estradiol and progesterone. There is evidence for the existence of receptors for both estrogen and progesterone in the adenohypophysis, the hypothalamus, as well as in higher brain centers. Changing occupancy of all these receptors by estrogen and progesterone could have the consequence of modulating the ratio of FSH to LH which is secreted.

The dominant hormonal changes of the menstrual cycle, particularly on the uterine endometrium, are mediated by the steroid hormones secreted by the ovaries and corpus luteum. Associated with the cyclical changes in the gonadotropins described above are related changes in the blood levels of estrogen and progesterone. In the early preovulatory phase, estradiol levels remain low until ~7–8 days before the LH surge characterizing ovulation (day 14). Then estradiol increases and reaches a peak 1 day before the LH surge. During the postovulatory phase, there is a drop of estradiol at days 14–16 followed by a rise to a second peak at day 22–23.

Progesterone secretion by the ovaries in the follicular period is very low and accordingly the blood levels are low. Some additional progesterone is produced by the adrenals. The blood levels of progesterone rise dramatically in the luteal period after ovulation and peak at days 18–24 of the cycle. This rise and peak coincides with maximal steroid hormone synthesis of the corpus luteum. The blood levels of both progesterone and estradiol fall after day 24 until initiation of menstruation. If fertilization occurs, the corpus luteum is rescued and continues the production of progesterone until the placenta becomes functional.

In the ovary, the follicle matures and the corpus luteum develops. In a select follicle, at the beginning of the cycle, the oocyte becomes progressively larger and the surrounding granulosa cells proliferate. The granulosa cells produce principally only estradiol. The cells adjacent to the follicle become enlarged and arranged in concentric circles in a cellular array termed the theca. The theca cells are active in steroid metabolism and can produce both estradiol and androstenedione. As the follicle develops, the granulosa cells produce, due to the trophic actions of FSH, increasing amounts of estradiol. Blood levels of estradiol increase slowly and then more rapidly to reach an apex just prior to the LH surge. This increase has the effect of establishing the high levels of estradiol required for positive feedback at the hypothalamus and pituitary level. Simultaneously, receptors for LH are appearing in increasing concentration on both the thecal and granulosa cells in preparation for ovulation. Very late in the follicular phase, after blood levels of LH are greater than blood levels of FSH, the thecal cells are stimulated by LH to begin producing progesterone. The general maturation of the follicle is complete and it is referred to as a graafian follicle.

After ovulation, both the thecal and granulosa cells of the follicle undergo rapid mitosis. Out of the follicle a new endocrine organ is created, the corpus luteum. The corpus luteum reaches its maximum size by the middle of the luteal phase, and if fertilization does not occur it undergoes regression and degeneration. The corpus luteum under the stimulus of LH actively produces progesterone.

The uterine endometrial epithelium undergoes morphological changes throughout the 28 days of the menstrual cycle. During the first half of each menstrual cycle, when estrogen concentrations gradually increase to reach a maximum 24 hr before ovulation and while progesterone concentrations are relatively low, the endometrium is stimulated to increase in thickness. Then 36 hr after ovulation, when the progesterone concentration rises sharply due to its secretion from the corpus luteum and estrogen levels are maintained at levels two-thirds of their previous maximum, further specific morphological changes are induced in the endometrium. There is stromal edema, glandular secretion, and vascularization. In the event that fertilization does not occur, the stromal edema decreases, glandular secretions diminish, and vascularization ceases. At the time of the rapid fall in estrogen and progesterone at the end of the luteal phase, blood stasis and stromal degeneration occur and the endometrial tissue is sloughed off.

The steroid contraceptive pill is the most widely used method of contraception; worldwide some 50 million women take some form of oral contraceptive. The most common of the presently employed synthetic oral contraceptives is composed of tablets containing both a progestin and an estrogen. Contraceptive steroids prevent ovulation by interfering with the release of GnRH by the hypothalamus and LH and FSH by the pituitary and thus block the midcycle surge of gonadotropins which mediate ovulation.

Estrogen is seen to play a central role in normal female physiology. The dominant actions of estrogen occur in the female reproductive tract, although there are also significant biological actions mediated in the pituitary, hypothalamus and brain as well as in a variety of other visceral organs. Estrogen receptors are distributed among a number of tissues, including uterus, vagina, placenta, oviduct, ovary, corpus luteum, mammary tissue, pituitary, hypothalamus, brain, liver, kidney, lung, bone, etc. The presence of estrogen receptors in a tissue presumes biological actions of estrogen at that location. Indeed, an effect by estrogen in bone has recently been explained (see infra).

In female pathology, a connection between estrogen and cancer, for example, breast and uterine cancer, is well documented but poorly understood. An association between estrogen receptor action and infertility has been suggested. Estrogen is important in protection against osteoporosis and cardiovascular disease, albeit via unknown mechanisms.

Hormone replacement therapy for the reversal of changes associated with decreased levels of estrogen as characterizes menopause has certain risks and benefits. Gambrell, R. D., *American Family Physician* 46: 87S–96S (1992); Harlap, S., *Am. J. Obstet. Gynecol.* 166: 1986–1992 (1992); Whitcroft and Stevenson, *Clinical Endocrinology* 36: 15–20 (1992). Estrogens are effective in postmenopausal women in reversing vasomotor symptoms and vaginal atrophy. Estrogens also prevent the bone loss associated with osteoporosis. Further, estrogens are known to reduce the risk of cardiovascular disease. Therapy unopposed by progesterone treatment, however, increases the risk of developing endometrial cancer, breast cancer, and, possibly, certain other cancers.

Post-menopausal osteoporosis affects 1.5 million women each year, making this disease a major health care problem. Horowitz, M. C. *Science* 260: 626–627 (1993). The pathological bone loss underlying this disorder can be prevented by estrogen replacement therapy. The mechanism by which estrogen exerts its bone sparing effect is unclear. Recent advances, however, indicate that estrogen regulates the circuitry of cytokine action that controls bone remodeling.

In normal bone remodeling, bone resorption by osteoclasts is balanced against bone formation by osteoblasts. Osteoclast mediated bone resorption can be influenced by two processes: activation, in which the resorptive function of mature osteoclasts is increased, and recruitment, in which osteoclast progenitors are stimulated to become mature cells. Activation occurs when certain cytokines, such as parathyroid hormone (PTH) or peripheral blood monocyte (PBM)-derived interleukin-1 (IL-1) or tumor necrosis factor (TNF), stimulate osteoblasts to secrete other cytokines that act on osteoclasts to cause bone resorption. In recruitment, still other cytokines are required for the maturation of progenitors into osteoclasts. These cytokines, such as macrophage-colony stimulating factor (M-CSF) and interleukin-6 (IL-6), are secreted by stimulated osteoblasts, while other cytokines, such as granulocyte macrophage-colony stimulating factor (GM-CSF), are secreted by PBMs.

It is believed that with estrogen acting as the inhibitor, PBMs serve as a source of limited quantities of IL-1, TNF, and GM-CSF, and osteoblasts secrete small amounts of M-CSF and IL-6. In this way, normal bone remodeling is maintained. The absence of estrogen is thought to cause PBMs to increase secretion of IL-1, TNF, and GM-CSF. Osteoclast activation and differentiation are thereby enhanced. Normal bones can consequently become osteoporotic.

In the estrogen deficient situation, a direct role for osteoblasts is also postulated. Osteoblasts probably secrete more IL-6, causing increased osteoclast differentiation, and probably also produce-more activating cytokines that directly activate osteoclasts. Bone resorption is presumably augmented, and osteoporosis ensues. The finding that estrogen receptors are expressed by macrophages and bone cells (Eriksen et al., *Science* 241: 84–86 (1988) (osteoblasts); Pensler et al., *J. Bone Mineral Res.* 5: 797–802 (1990) (osteoclasts)) corroborates the theory that estrogens exert osteoporotic effects by regulating bone cell cytokines.

The classical strategy for the identification of endocrine glands and hormones has been ablation of the suspected tissue, which should produce deficiency symptoms, followed by replacement of the ablated tissue, which presumably reverses the deficiency symptoms. The study of steroid hormones, including sex hormones, such as the estrogens, has profited by the application of such methods. Nevertheless, a modern approach, tailored to address the regulatory capacity of the steroid receptor in physiological responses, is needed to supersede the classical.

In particular, a need exists for an animal model system to study the biological role of hormones, including steroid hormones and sex steroids, like the estrogens, in growth, development, morphological differentiation, sexual and reproductive behavior and cycles, etc. Such an animal model system should provide a means for testing sex hormones and synthetics that mimic or antagonize sex hormones for use in birth control methods. It should also facilitate evaluation of hormone replacement therapies that raise questions about risks and benefits. The animal model system should be amenable to characterization of materials suspected of precipitating or conferring protection against, e.g., osteoporosis, cardiovascular disease, breast cancer, endometrial cancer, and other cancers, and thus contribute to diagnosis, prognosis, and therapy of these major diseases. Accordingly, it is an object herein to provide certain mutant non-human vertebrates having a deficit of functional steroid hormone receptors, and related methods and constructs.

SUMMARY OF THE INVENTION

According to the invention, there is provided a mutant non-human vertebrate, in which all or some of the germ and somatic cells contain a mutation in at least one steroid hormone receptor allele, which mutation is introduced into the vertebrate, or an ancestor of the vertebrate, at an embryonic stage, and which mutation produces a phenotype in the vertebrate characterized by a deficit of functional steroid hormone receptors encoded by the allele.

The vertebrate may be one in which all of the germ and somatic cells contain the mutation, i.e., the vertebrate is a heterozygote or a homozygote for the mutation. Or the vertebrate may be one in which all of the germ and somatic cells contain the mutation, wherein both of the steroid hormone receptor alleles contain the mutation, i.e., the vertebrate is a homozygote for the mutation. Or the vertebrate may be one in which only some of the germ and somatic cells contain the mutation, i.e., the vertebrate is a chimera.

The steroid hormone may be estrogen. The vertebrate may be a rodent, and the rodent may be a mouse. The mutation may be introduced by at least one embryonic stem cell containing the mutation. The mutation may be introduced by homologous recombination. The mutation may be introduced by a DNA construct comprising DNA of a gene encoding the steroid hormone receptor and a mutation contained therein. The mutation may comprise disruption of the DNA by DNA encoding a marker that permits positive selection. The DNA construct may further comprise DNA encoding a marker than permits negative selection.

According to another aspect of the invention, there is provided a method of producing a mutant non-human vertebrate, in which all or some of the germ and somatic cells contain a mutation in at least one steroid hormone receptor allele, which mutation produces a phenotype in the vertebrate characterized by a deficit of functional steroid hormone receptors encoded by the allele, comprising the step of: (a) introducing the mutation into the vertebrate, or an ancestor of the vertebrate, at an embryonic stage.

The method may be one wherein all of the germ and somatic cells of the vertebrate contain the mutation, and wherein the mutation was introduced into an ancestor of the vertebrate at an embryonic stage, further comprising the steps of: (b) transplanting the ancestor at an embryonic stage into a pseudopregnant mouse, (c) allowing the ancestor to develop to term, (d) identifying at least one mutant ancestor, in which at least some of the germ and somatic cells contain the mutation, and (e) breeding the ancestor to form a mutant non-human vertebrate, in which all of the germ and somatic cells contain the mutation (i.e., the vertebrate is a heterozygote or a homozygote for the mutation).

The method may be one wherein all of the germ and somatic cells of the vertebrate contain the mutation, and wherein both of the steroid hormone receptor alleles of the vertebrate contain the mutation, further comprising the step of: breeding a mutant non-human vertebrate, in which all of the germ and somatic cells contain the mutation in at least one steroid hormone receptor allele, to another mutant non-human vertebrate, in which all of the germ and somatic cells contain the mutation in at least one steroid hormone receptor allele, to form a mutant non-human vertebrate, in which all of the germ and somatic cells contain the mutation in both of the steroid hormone receptor alleles (i.e., heterozygotes for the mutation are bred to form a homozygote for the mutation).

The method may be one wherein all of the germ and somatic cells of the vertebrate contain the mutation, and wherein both of the steroid hormone receptor alleles of the vertebrate contain the mutation, further comprising the step of: introducing a second mutation into the vertebrate, or an ancestor or the vertebrate, at an embryonic stage, so as to produce the mutation in both of the steroid hormone receptor alleles (i.e., the vertebrate is homozygous for the mutation).

The method may be one wherein only some of the germ and somatic cells of the vertebrate contain the mutation, and wherein the mutation is introduced into the vertebrate at an embryonic stage, further comprising the steps of: (b) transplanting the vertebrate at an embryonic stage into a pseudopregnant mouse, (c) allowing the vertebrate to develop to term, and (d) identifying at least one mutant non-human vertebrate, wherein only some of the germ and somatic cells contain the mutation (i.e., the vertebrate is a chimera).

The method may be one in which the steroid hormone is estrogen. It may be one in which the vertebrate is a rodent, and the rodent may be a mouse. The method may involve introducing the mutation by introducing at least one embryonic stem cell containing the mutation into the vertebrate or an ancestor of the vertebrate. The method may feature introducing the mutation by homologous recombination. The method may encompass introducing the mutation by introducing a DNA construct comprising DNA of a gene encoding the steroid hormone receptor and a mutation contained therein; the mutation may comprise disruption of the DNA by DNA encoding a marker that permits positive selection; and the DNA construct may further comprise DNA encoding a marker than permits negative selection.

According to yet another aspect of the invention, there is provided a construct adapted for use in introducing into cells of a vertebrate a mutation in at least one steroid hormone receptor allele, the construct comprising: DNA of a gene encoding the steroid hormone receptor and a mutation contained therein. The mutation may comprise disruption of the DNA by DNA encoding a marker that permits positive selection. The construct may further comprise a promoter operably linked to the marker-encoding DNA; it may further comprise a polyadenylation signal that facilitates expression of the marker-encoding DNA. The marker may confer resistance to G418. The promoter may be derived from phosphoglycerate kinase. And the polyadenylation signal may be derived from phosphoglycerate kinase.

The construct may further comprise DNA encoding a marker that permits negative selection. It may further comprise a promoter operably linked to the marker-encoding DNA, which marker permits negative selection. This marker may comprise a gene encoding herpes simplex thymidine kinase, and the promoter may be derived from phosphoglycerate kinase. The steroid hormone may be estrogen.

The invention also provides embryonic stem cells containing any of the constructs described above; and embryonic stem cells containing a mutation in at least one steroid hormone receptor allele, which mutation results in a deficit of functional steroid hormone receptors encoded by the allele, and which mutation is introduced by any of the constructs above described.

The invention further provides blastocysts containing the embryonic stem cells described supra.

Also provided by the invention are cells of any of the mutant non-human vertebrates described above, containing the mutation.

According to still another aspect of the invention, there is provided a method for testing a material suspected of facilitating or precluding a condition, comprising the steps of: (a) administering the material to any of the mutant non-human vertebrates described supra; and (b) measuring the effect on the vertebrate. The condition may be cancer, osteoporosis, cardiovascular disease, or pregnancy.

BRIEF DESCRIPTION OF THE DRAWING

FIG. 1A is a map of the target locus, including exon 2 and surrounding sequences. FIG. 1B depicts the targeting vector, which contains a neomycin gene (NEO) inserted into the estrogen receptor second exon and a herpes simplex thymidine kinase gene (TK) to allow counter selection. FIG. 1C represents integration, via homologous recombination, into the target locus to disrupt the estrogen receptor gene. The right angle arrow indicates the position of the ATG start site in exon 2 and the orientation of the resultant ER transcript. The numbered arrow heads identify PCR primers and their sequence positions as discussed in Example 1. Restriction sites are as follows: B, Bam HI; H, Hind III; N, Not 1; S, Spe 1.

DETAILED DESCRIPTION OF THE INVENTION

The present invention provides certain mutant non-human vertebrates having a deficit of functional steroid hormone receptors, and related methods and constructs. These mutants are provided to satisfy the need existing for an animal model system to study the biological role of hormones, including steroid hormones and sex steroids, like the estrogens, in growth, development, morphological differentiation, sexual and reproductive behavior and cycles, etc. Such an animal model system provides a means for testing sex hormones and synthetics that mimic or antagonize sex hormones for use in birth control methods. It also facilitates evaluation of hormone replacement therapies that raise questions about risks and benefits. The animal model system is amenable to characterization of materials suspected of precipitating or conferring protection against, e.g., osteoporosis, cardiovascular disease, breast cancer, endometrial cancer, and other cancers, and thus contributes to diagnosis, prognosis, and therapy of these major diseases.

"Knockout" animals in which genes have been mutated to prevent expression of functional protein products represent a modern approach that supersedes the classical strategy to the identification of endocrine glands and hormones by ablation and replacement. However, making knockouts "is far from a cookbook procedure." Baringa, M., *Science* 257: 1046–1047 (1992). Moreover, the odds of success at generating knockout animals that have a deficit of functional steroid hormone receptors, particularly estrogen receptors, are generally regarded as poor (George, F. W. and Wilson, J. D. in *The Physiology of Reproduction*, Knobil et al., editors (Raven Press, Ltd., New York, 1988)). The lack of reported human estrogen receptor mutations has suggested that, if they do occur, the estrogen receptor mutations are lethal (Id.). Nevertheless, in a particularly preferred embodiment, Applicants provide herein viable mice with an inhibition of estrogen receptor, responsiveness by targeted disruption of the estrogen receptor gene.

The mutants of the invention constitute non-human vertebrates. The term "vertebrate" encompasses mammals, birds, reptiles, amphibians, and fishes that possess steroid hormone receptors. Steroid hormones include estrogens (such as estradiol), mineralocorticoids (such as aldosterone), glucocorticoids (such as cortisol), androgens (such as testosterone), and progestins (such as progesterone). Steroid hormone receptors have been demonstrated in all species of vertebrates. For example, estrogen receptors have been cloned from vertebrates such as mouse (White et al., *Molecular Endocrinology* 1: 735–744 (1987)), rat (Koike et al., *Nucleic Acids Res.* 15: 2499–2513 (1987)), chicken (Krust et al., *EMBO J* 5: 891–897 (1986)), trout (Paklel et al., *Mol. Cell. Endocrinol.* 71: 195–204 (1990)), and human (Green et al., *Nature* 320: 134–139 (1986)), etc. Sequences encoding mineralocorticoid receptors have been obtained from vertebrates, including rat, (Patel et al., *Molecular Endocrinology* 3: 1877–1885 (1989)) and human (Arriza et al., *Science* 237: 268–275 (1987)). So, too, have sequences for glucocorticoid receptors been derived from vertebrates, like mouse (Danielsen et al., *EMBO J* 5: 2513–2522 (1986)) and human (Hollenberg et al., *Nature* 318: 635–641 (1985)). Cloning of androgen receptors has been realized using vertebrates such as rat (Chang et al., *Science* 240: 324–326 (1988)) and human (Id.; Lubahn et al., *Science* 240: 327–330 (1988)). Progesterone receptors have been the subject of successful cloning attempts using vertebrates including chicken (Conneely et al., *Science* 233: 767–770 (1986); Jeltsch et al., *Proc. Natl. Acad. Sci. USA* 83: 5424–5428 (1986)), rabbit (Loosfelt et al., *Proc. Natl. Acad. Sci. USA* 83: 9045–9049 (1986)) and human (Misrahi et al., *Biochem. Biophys. Res. Commun.* 143: 740–748 (1987)). Rodents, including rats and mice, especially mice, embody preferred vertebrates of the invention. Receptors for estrogen represent preferred steroid hormone receptors as these fall within the scope of the invention.

The mutant non-human vertebrates featured by the invention are vertebrates in which all or some of the germ cells and somatic cells contain a mutation in at least one steroid hormone receptor allele. The mutation is introduced into the vertebrate, or an ancestor of the vertebrate, at an embryonic stage. The mutation produces a phenotype in the vertebrate characterized by a deficit of functional steroid hormone receptors encoded by the allele. Germs cells are generally defined as gametes or their precursors, somatic cells as cells that are not germ cells. A mutation may be introduced at any embryonic stage of development, including fertilized oocyte, zygote, morula, blastocyst, etc.

Various methods of producing mutations are contemplated and well known in the art. Preferred is a method where a mutation is generated in a hormone receptor allele by the introduction of a DNA construct containing DNA of a gene encoding a steroid hormone receptor and the mutation accommodated therein. The mutation is targeted to the allele by way of the DNA construct. The DNA of the gene encoding the steroid hormone receptor contained by the construct may be foreign to the species of which the recipient is a member, as in exogenous DNA, or native to the species and foreign only to the individual recipient, as in isogenous DNA, or a mixture of both. The mutation may constitute an insertion, deletion, substitution, or combination thereof. The DNA construct can be introduced by, for example, calcium-phosphate DNA co-precipitation, It is preferred that a mutation be introduced into a electroporation, microinjection, virus infection, ligand-DNA conjugation, virus-ligand-DNA conjugation, and liposomes.

It is preferred that a mutation be introduced into a vertebrate, or an ancestor thereof, by the introduction into the vertebrate, or its ancestor, of a certain kind of cell or cells containing the mutation. These cells are pluripotent and undifferentiated. They are advantageously capable of being maintained in vitro and, upon being returned to embryos, of differentiating and contributing to the germ line of the resultant adult. Embryonic stem (ES) stems, derived from embryos, and embryonic carcinoma (EC) cells, originating from teratocarcinomas, are examples of such cells. While ES and EC cells derived from vertebrates of every species are contemplated, embryonic stem cells originating from rodents, especially mouse, are preferred.

Rodent (e.g., mouse) embryonic stem cells may be freshly established from blastocysts of the inner cell mass of pre-implantation embryos (e.g., mouse strain 129) or maintained as permanent cell lines. Generally, male (XY) embryonic stem cells are preferred. The pluripotent and undifferentiated state of ES cells may be preserved by culturing them in medium supplemented with leukemia inhibitory factor (LIF) or by co-culturing them with mitotically inactive feeder cells such as irradiated primary fibroblasts or fibroblast cell lines. Detailed methods for isolating, culturing and characterizing embryonic stem cells have been well described (Mansour, S. L., *GATA* 7: 219–227 (1990)).

It is contemplated by the present invention that ES cells be manipulated while being maintained in culture. ES cells can be mutagenized by, for example, the introduction of DNA constructs while they survive in tissue culture plates or flasks. Populations of ES cells can be screened in vitro to select for cells harboring specific genetic mutations. Cells surviving selection can be cloned and maintained as pure populations. Clones can be induced to differentiate in vitro or introduced into embryos, advantageously by aggregation within morulae and preferably by injection into blastocysts (e.g., mouse strain C57BL). The embryo can be implanted in the uterus of a pseudo-pregnant foster mother and permitted to develop to term. The resulting animal may be derived entirely from stem cells or may be chimeric, that is mosaic, in that it is composed of cells derived from both the donor stem cells and the host blastocyst. Chimeric founders can be crossed, for example, with wild types to produce heterozygotes for the mutation. Mutant animals may be made homozygous for the mutation by the interbreeding of, for instance, heterozygotes. Alternatively, homozygosity for a mutation in both alleles may be produced by using, e.g., an ES cell with one mutated allele into which is introduced a second mutation. Such a second mutation, resulting in having both copies of the gene mutated, may be the same or different from the first mutation.

Chimeras and progeny of chimeras that originate from ES cells may be readily detected by combining donor stem cells with host blastocysts that differ phenotypically. For example, donor embryonic stem cells may be derived from a mouse having an agouti colored coat, i.e., the black hairs carry a subapical yellow band that causes the hair to appear brownish or tan. The host blastocyst may be obtained from a mouse with hair color that is solid black due to a recessive mutation at the agouti locus, which prevents formation of the yellow band. The fur of resultant chimeric mice will conveniently have patches of both colors, agouti and black, because the mouse contains cells of both genotypes. Breeding of the chimeras (preferably males) with, for example, mice (females) having hair color that is solid black will statistically yield some mice that have pure agouti colored coats and other mice that have pure black coats. Any offspring that have the dominant agouti coat color are derived from the ES genome. Genetic screening of these progeny may subsequently be used to determine which mice received the allele containing the mutation, i.e. which are heterozygous for the mutation.

The mutant non-human vertebrates of the invention feature a mutation at a particular location in the genome, specifically an allele encoding asteroid hormone receptor. According to a preferred embodiment, the mutation is site-directed to the gene of interest by way of a DNA construct. Site-directed mutagenesis is preferably accomplished by way of homologous recombination between the particular genomic location and that part of the DNA construct containing DNA of a gene encoding the steroid hormone receptor with the mutation accommodated therein.

The particular composition of the DNA construct may determine the specific outcome of the target event. For example, a single-step "O-type" insertional event can involve an O-type targeting construct having a double strand cut within a region of sequence identity. The construct may contain a selectable marker gene. By way of a single cross-over, the insertional event tends to produce an insertion accompanied by duplication of the homologous region of sequence. In contrast, a single-step "m-type" replacement event can entail an m-type DNA construct with a region of sequence identity interrupted by a loop of non-homologous DNA, which may, e.g., contain a selectable marker gene. Due to double cross-over, the replacement event may generate replacement of chromosomal sequences by the incoming DNA, an insertion, or a deletion. In any case, a duplication does not tend to result from this kind of event. By comparison, a two-step, "in-out" targeting event for replacing chromosome segments with altered DNA sequences can feature an O-type DNA construct with a modification and a double strand cut contained in a region of sequence identity. The construct optionally includes a selectable marker gene. The "in" step tends to generate an insertion of the modification accompanied by a duplication of the homologous region of sequence by an O-type event. The "out" step tends to involve an excision cross-over resulting in retention by the chromosome of the modification while the duplicated sequence is eliminated.

Any of those DNA constructs that bring about the site-directed mutations of the present invention are contemplated as falling within its scope. Advantageous are constructs that facilitate homologous recombination, e.g., constructs that contain a region of sequence homologous to a region in the target gene containing therein the modification to be introduced. Constructs of the O-type and $\Omega$-type and those that facilitate targeting events that are single step and multiple step, and that comprise insertions, replacements, and deletions, and that involve single cross-overs and multiple cross-overs, and any combination of these constructs are embraced.

A replacement-type vector is preferred, i.e., where a region of sequence identity is interrupted by a loop of non-homologous DNA. In this case, the homologous sequence serves to target the mutation and the nonhomologous DNA operates as the mutation, for example, an insertion. The region of sequence identity should include a sufficient number of bases and of sufficient identity to permit homologous recombination, that is, site-directed, as opposed to random, integration into a host genome. See, e.g., Kucherlapati, Koller, and Smithies, International Application No. PCT/US90/04178 (WO91/01140), published Feb. 7, 1991. An empirical approach needs to be taken when constructing vectors that facilitate homologous recombination, as regions of a gene that are recombinogenic may be identified only upon experimentation. Such experimentation is well within the skill of workers in this art.

Regions of sequence identity may be obtained from genes that have been isolated from genomic sources, by preparation of cDNAs from isolated mRNA templates, by direct synthesis, or by some combination thereof. The published sequences of numerous steroid hormone receptor genes greatly facilitates the obtaining of homologous sequence for the targeting of certain genes. This invention is not limited to the use of any particular steroid hormone receptor gene. However, the gene encoding the estrogen receptor is preferred, particularly the gene derived from rodents, including rats and mice, especially mice. The mouse estrogen receptor cDNA has been cloned and the sequence published (White et al., *Molecular Endocrinology* 1: 735–744 (1987)). So, too, has the genomic sequence encoding the mouse estrogen receptor been cloned and published (Id.).

Regions of non-identity constituting lesions, e.g., insertions, will normally be positioned within a portion of the coding sequence, that is, within one or more exons, and may occur within one or more introns, for example, within flanking non-coding regions, such as 5' non-coding regions, which form transcriptional regulatory regions. Where such mutations constitute insertions, they should be of sufficient length and structure so as not to interfere with homologous recombination.

Where a region of non-homologous DNA operates as a mutation, for example, an insertion, it may contain a selectable marker to identify the integration of a target construct into a host genome. A marker may be employed that facilitates positive selection, that is, integration is indicated by the presence (versus the absence) of a gene undergoing expression. Positive selection markers that may be used include the hygromycine B resistance gene, the neo gene, and hprt gene. Preferred is a gene conferring antibiotic resistance, especially, the neomycin resistance gene permitting G418 selection. Choosing different (for example) neo cassettes is empirical, as selectable markers such as neo are not expressed at all integration sites due possibly to position effects on transcription. Such determinations are well within the level of skill in the art.

A targeting vector may be optimized by including a negatively selectable marker upstream and/or downstream of (i.e., flanking) the region of homology. Negative selection permits enrichment of cells surviving selection as a consequence of homologous recombination rather than random integration. It is conjectured that the negatively selectable gene is eliminated in homologous crossovers by virtue of being situated outside the region of homology. Thus, cells incorporating the negatively selectable gene are cells that have promiscuously participated in nonhomologous integration. These cells will be killed by the negative selection. In contrast, cells that have enjoyed only homologous recombination will be free of the negatively selectable gene. These, the desired cells, will survive the negative selection protocol. Genes facilitating negative selection include genes that are toxic to cells upon expression, like diphtheria toxin A gene. The herpes simplex thymidine kinase (HSVtk) gene may have particular utility. Cells with a copy of this gene can be selectively killed by supplying them with nucleoside analogs, such as ganciclovir or acyclovir or FIAU (1-(2-dexoy 2-fluoro-β-D-arabinofluranosyl)-5-iodouracil), which the cells convert into toxic intermediates during DNA synthesis.

Positive-negative selection schemes represent preferred embodiments of the invention, as these schemes fall within its scope. Enrichment of cells is contemplated in which there is positive selection for cells surviving, e.g., G418, together with negative selection against cells killed by, for example, ganciclovir. Other positive-negative selection protocols are also available.

The DNA constructs of the invention may be modified to include other entities that are useful in the preparation of the construct, amplification, introduction into the recipient cell, and integration of sequence into the host cell DNA. For example, they may include a replication system for prokaryotes, like E. coli, for use in preparing the construct, cloning after each manipulation, allowing for analysis, expansion of a clone and isolation of a plasmid for subsequent manipulation. Prokaryotic sequences may be removed before introduction of the DNA construct into target eukaryotic cells.

The DNA construct may further include a replication system which is functional in the host eukaryotic cell. These replication systems may be derived from eukaryotic-cell infecting viruses, for example, Simian Virus 40, Epstein-Barr virus, papilloma virus, adenovirus and the like. Extraneous sequences can be eliminated, the construct linearized, etc., before insertion into target cells.

Where a selectable marker gene is employed, it may include transcriptional regulatory regions, especially transcriptional initiation regulatory regions, such as promoters and enhancers. These regions may be native to the species from which the selectable marker gene is derived or foreign.

Promoters and enhancers that can be recognized by the transcriptional initiation machinery of the host eukaryotic cell are particularly useful. These regions may be constitutive or inducible. Select promoters include SV40 early and late, MMTV LTR, RSV LTR, Adenovirus 2 major late, CMV immediate early, HSVtk, and mammalian metallothionein-I and II, and enhancers such as those derived from SV40, RSV, and CMV are noteworthy. Strong promoters, such as the phosphoglycerate kinase (PGK) promoter, the RNA polymerase II (Pol 2) promoter, and the mutated polyoma enhancer/HSVtk promoter combination (Koller, B. H. and Smithies. O., Annu. Rev. Immunol. 10: 705–730 (1992)) are preferred for driving the selectable marker genes of the invention.

Other DNA sequences and segments that facilitate expression of selectable marker genes may be incorporated into the DNA constructs of the present invention. These sequences and segments may constitute regions of DNA that regulate transcription, including initiation and termination of transcription, translation, including its initiation and termination, processing of transcripts, post-translational modification, etc. Such regions include, by way of example only, intron splicing junctions, ribosome binding sites, and polyadenylation signals. Optimization of expression by selection of these features is well within the skill of the art. The poly A addition site derived from SV40 early and late genes, and especially the phosphoglycerate kinase (PGK) polyadenylation signal, is found to be maximizing for stabilization, localization and processing of expressed messages.

Cells isolated from live animals may be analyzed to corroborate the occurrence of a gene targeting event mediated by the introduction of a DNA construct into a host cell. For example, restriction mapping, Southern hybridization assays, and the like may be performed. The polymerase chain reaction is especially useful for this purpose. By choosing appropriate primers for the PCR reaction, it is possible to screen cells for site-directed mutagenesis between vector and target based on the production of a new junction fragment. Conveniently, one primer is chosen to be complementary to sequences specific to the incoming DNA located on the vector. A second primer is chosen to be complementary to sequences specific to the target. Only when the two primers are juxtaposed, as they are following gene targeting, is efficient amplification of the recombinant fragment possible. As will be appreciated by those with ordinary skill in the art, these and other assays may be used for the diagnosis of chimeras, heterozygotes, and homozygotes for the mutation.

The mutant non-human animals of the invention manifest a phenotype that is the result of a mutation in at least one allele contained in at least one cell and that is characterized by a deficit of functional receptor proteins encoded by that allele. The deficit is meant to encompass not only a complete lack but also a substantial absence of receptors capable of mediating steroid hormone responsiveness. This deficit may occur due to a shortage of the wild type gene product. Alternatively, it may arise out of the production of a mutant form of the protein. Still another alternative is a combination of these possibilities. All of these embodiments are contemplated as falling within the scope of the invention. Indeed, the deficit may be the consequence of events transpiring at any of numerous stages along the biosynthetic pathway leading to the formation of a mature protein, such as transcription, processing of the message, translation, post-translational modification, etc.

The shortage of a wild type protein and the production of a mutant form may be detected in a variety of ways known to those in the art, including Northern hybridization assays, Western blotting, conventional immunoassay methods, DNA binding experiments (e.g., gel mobility shift assays, DNA footprinting assays), dimerization experiments, ligand binding experiments, transcription activation experiments, FACS analyses and the like. Accordingly, for example, a mutant having a deficit of functional estrogen receptor proteins may be identified by immunoassay techniques employing monoclonal antibodies specific to receptor antigens using, for instance, tissue from female reproductive tract. Loss of activity may be corroborated by, e.g., estrogen binding experiments.

Additionally, the chimeras, heterozygotes, and homozygotes of the invention can be observed or tested in comparison to wild type animals to ascertain an inhibition in steroid hormone responsiveness. The mutants may be recognized by anatomical or physiological examination of the cells, tissues, organs, or systems comprising them. The external characteristics of the animal can be scrutinized, as can the internal, by gross inspection or histological investigation. In vitro, in vivo, and in situ bioassays can be conducted to detect the activity of hormone receptor proteins. Experiments can be performed to test for behavior known to be mediated by hormones.

Thus, for example, a suspected knock-out for the estrogen hormone receptor can be probed and dissected. Sexual development may be established. Sterility can be determined. Gross or histological observation of the female reproductive tract may reveal ovaries that are hyperstimulated possibly due to the sustained action of gonadotropins that have presumably failed to undergo negative feedback by estrogens due to the apparent deficit of operational estrogen receptors. Treatment with classical estrogen stimulants can be used to measure the effects on reproductive tissues and mating behavior. In this way, mutants having the phenotype in question may be distinguished.

The vertebrates, constructs, cells, tissues, organs, systems, chimeras, heterozygotes, homozygotes and methods of the invention have multiple uses, as provided herein. For example, the animals of the invention can be used to test non-steroidal hormone materials suspected of facilitating or precluding conditions that are known or believed to be associated with steroid hormones. These conditions include growth and morphological development, sexual differentiation, fertility, and pathophysiologies such as cancer, osteoporosis and cardiovascular disease.

For example, the mutants of the invention that have a deficit of estrogen receptors will be more susceptible to osteoporosis, atherosclerosis and cardiovascular disease. Without being able to respond to the estrogen that protects against these disorders, the animals are rendered more vulnerable. Analogously, the onco-mammals of U.S. Pat. No. 4,736,866, being transgenic for oncogenes, have a propensity toward cancer. These onco-mammals provide a model system for the testing with increased sensitivity of materials suspected of causing or conferring protection against cancer. Likewise, the mutants of the invention constitute animal models for the measurement with enhanced accuracy and precision of substances believed to precipitate or prevent osteoporosis, atherosclerosis, and cardiovascular disease.

Additionally, the elimination of, for example, the estrogen hormone variable, has value in the assessment of non-estrogenic factors underlying diseases such as breast cancer, uterine cancer and other cancers that are linked with estrogen. The animals of the invention accordingly constitute valuable model systems for the evaluation of non-estrogen type compounds for an effect in causing different kinds of cancers or conferring protection against them. This effect is less likely to be amenable to characterization, i.e., to be missed, in an estrogen responsive system.

Furthermore, the animals of the invention having a deficit of estrogen hormone receptors can serve in the discovery of non-estrogenic drugs that act in birth control or fertility. For instance, substances that mimic or antagonize follicle stimulating hormone, luteinizing hormone or gonadotropin releasing hormone may have utility as non-steroidal birth control agents or in the induction of fertility. By eradicating the role played by estrogen in the animal model systems of the invention, the unknowns tested in a drug discovery program will be more properly classified.

To test for a material suspected of causing a condition, the vertebrates of the invention are exposed to the material and then evaluated for a response. For example, the determination of neoplasia, bone loss and cardiovascular lesions will be indicative of cancer, osteoporosis and cardiovascular disease, respectively. Animals that are aged and thus presumed especially susceptible to developing bone disease and circulatory disorders, are particularly suitable for assessing materials thought to be only weakly causative of osteoporosis, atherosclerosis, or cardiovascular illness. By studying the onset, nature and extent of the effect, the test material can be even more thoroughly characterized.

Alternatively, the animals provided herein can be used to test substances for the ability to confer protection against the development of conditions, such as pregnancy or cancer, osteoporosis or cardiovascular disease. After treating the animals with a test substance, the reaction as compared to untreated controls is appraised. A comparatively lower incidence of neoplasia, bone loss or myocardial infarction or stroke, etc. in the treated animal is considered as an indication of protection. Similarly, a relatively low number of live births may reflect the discovery of a new birth control remedy. This method can further include administering known carcinogens to these animals, prior to, after, or simultaneously with treatment using putative anti-carcinogenic substances, and protection in an estrogen free environment determined.

Particular aspects of the invention may be more readily understood by reference to the following examples, which are intended to exemplify the invention, without limiting its scope to the particular exemplified embodiments.

EXAMPLE 1

MICE WITH INHIBITION OF ESTROGEN RECEPTOR RESPONSE BY TARGETED DISRUPTION OF ESTROGEN RECEPTOR GENE

Targeting Construct

The mouse estrogen receptor gene has been cloned and found to have nine exons (White et al., *Molecular Endocrinology* 1: 735–744 (1987)). Utilizing the published sequence and the polymerase chain reaction, two DNA fragments were amplified from the most N-terminal exon of the mouse estrogen receptor gene with oligonucleotide pairs 1–2 and 3–4 (see below). The two amplified fragments were used as probes to clone a 10 kb Bam HI fragment containing the second exon of the mouse ER gene from a Lambda Dash® (Stratagene, La Jolla, Calif.) library constructed from Bam HI digested DNA obtained from E14TG2a cells (mouse strain 129) (Hooper et al., *Nature* 326: 292–295 (1987)). To assemble the targeting construct (FIG. 1B), a neomycin gene (NEO) driven by the phosphoglycerate kinase (PGK) promoter and having a PGK poly A addition signal (Boer et al., *Biochemical Genetics* 28: 299–307 (1990)) was cloned in a 5' to 3' orientation into a Not I site within exon 2 contained in a 7.5 kb Bam HI/Spe I fragment, derived from the 10 kb Bam HI fragment, to disrupt the reading frame. A flanking herpes simplex thymidine kinase gene (HSVtk) driven by the same PGK promoter was added to the 3' end of the Bam HI/Spe 1 fragment (Mansour et al., *Nature* 336: 348–352 (1988)).

Because of difficulty in cloning of the 5' 7 kb Bam HI/Not I fragment, the targeting construct was assembled in a Lambda Dash® bacteriophage vector (Stratagene, La Jolla, Calif.). The neomycin gene/Not I/Spe I fragment and HSVtk gene were first cloned in pBluescript® (Stratagene, La Jolla, Calif.) and then subcloned into a Lambda Dash® vector (Stratagene, La Jolla, Calif.) containing the mouse estrogen receptor 7 kb Bam HI/Not I fragment. An internal Bam HI site in the neomycin gene was destroyed prior to cloning into the Lambda Dash® vector so that Bam HI could be used to remove the lambda arms as a prelude to electroporation.

The targeting construct is available in the laboratory of the named inventors.

Embryonic Stem Cells

The embryonic stem cell line E14TG2a (mouse strain 129/J) (Hooper et al., *Nature* 326: 292–295 (1987)) was cultured on primary embryonic fibroblast feeder layers previously irradiated with 3000 rads. The fibroblasts were isolated from neomycin resistant embryos (Koller et al., *Proc. Nat. Acad. Sci. USA* 88: 10730–10734 (1991)) and were resistant to G418 (Sigma, St. Louis, Mo.).

Electroporation

Electroporation of about $1 \times 10^7$ ES cells was performed in 0.5 ml of culture medium employing 5 nM targeting construct. The culture medium was composed of Dulbecco's Modified Eagle's Medium (DMEM), 15% fetal bovine serum, 0.1 mM 2-mercaptoethanol, and 2 mM glutamine. By using a 1 second discharge from a 150- to 250- µF capacitor charged to 250–400 V, the electroporation was effected. In early electroporations, the lambda arms were removed from the targeting construct, but in later ones, they were not removed.

Selection

After electroporation, the surviving cells were plated in 100 mm petri dishes and exposed for 10–14 days to 200 µg/ml G418 (Sigma, St. Louis, Mo.) and 1 µM ganciclovir (Syntex, Palo Alto, Calif.). Doubly resistant colonies were picked into 24-well plates and grown for 10 days. Subsequently, about one-tenth of a colony was replated into a single well of a 24-well plate, while the remainder of the colony was used to isolate DNA. The DNA isolated from four colonies was pooled and screened by PCR amplification for successful targeting (Kim et al., *Nucleic Acids Res.* 16: 8887–8903 (1987)).

PCR Primers

Oligo 1 was used for making the 5' probe to clone the ER gene:
5'-CGCTGCTGAGCCCTCTGCGTG-3'(SEQ ID NO:1).
Oligo 2 was used for making the 3' probe to clone the ER gene:
5'-GTTGAACTCGTAGGCGGCGCCCTC-3'(SEQ ID NO:2).
Oligo 3 was used for making the 5' probe to clone the ER gene and for determination of the presence of the wild type ER gene:
5'-CGGTCTACGGCCAGTCGGGCACC-3'(SEQ ID NO:3).
Oligo 4 was used for making the 3' probe to clone the ER gene and for determination of the presence of the wild type ER gene:
5'-GTAGAAGGCGGGAGGGCCGGTGTC-3'(SEQ ID NO:4).
Oligo 5, from sequence in the 3' end of the PGK gene, was used for determination of the presence of neomycin disruption of the ER gene:
5'-TTCCACATACACTTCATTCTCA-3'(SEQ ID NO:5).
Oligo 6, from sequence in intron 2 of the ER gene, was used for determination of the presence of neomycin disruption of the ER gene:
5'-CTCCACTGGCCTCAAACACCTG-3'(SEQ ID NO:6).

PCR Analysis

The 3' end of the PGK gene containing the poly A addition signal was sequenced. From this sequence, oligo 5 was designed for use in conjunction with oligo 6 to amplify a 649 bp fragment diagnostic of a successfully targeted ER gene (see FIG. 1). For PCR screening, DNA was obtained from pools composed of DNA extracted from four colonies of ES cells.

PCR screening was also used to distinguish normal, heterozygous and homozygous mutant animals. PCR reactions using primer set 5–6 amplified a 649 bp product specific for the disrupted gene. In contrast, PCR reactions using primer set 3–4 amplified a 239 bp product specific for the wild type ER gene. Thus, normal animals were identified by the presence of a PCR fragment using primer set 3–4 and the absence of a PCR fragment using primer set 5–6. Heterozygotes were distinguished by the presence of PCR fragments using both primer sets. Finally, homozygous mutant animals were characterized by the presence of a PCR fragment using primer set 5–6 and the absence of a PCR fragment using primer set 3–4.

Mouse Breeding

The targeted embryonic stem cells from strain 129/J mice were injected into blastocysts from C57BL/6J mothers. The embryos were returned to pseudopregnant C57BL/6J hosts to complete their development. Chimeras were determined by coat color, and males were bred to C57BL/6J wild type females. Tail DNA from agouti coat color F1 offspring was screened by PCR with primers 5 and 6 to ascertain successful targeting of the ER gene by detection of a 649 bp fragment. Heterozygotes were crossed and progeny screened by PCR for homozygosity. The F2 offspring and subsequent generations were screened by PCR with primers 5 and 6 to determine successful targeting of the ER gene as demonstrated by the presence of a 649 bp fragment, and with primers 3 and 4 to detect loss of the wild type gene as diagnosed by the absence of a 239 bp fragment.

Results

Figure 1A:
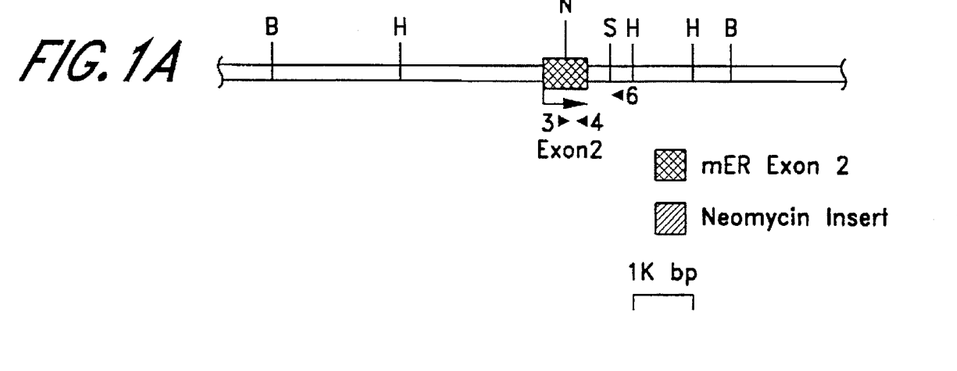
FIGS. 1A–1C illustrate targeted disruption of the estrogen receptor gene in the genome of the mouse.
Figure 1B:
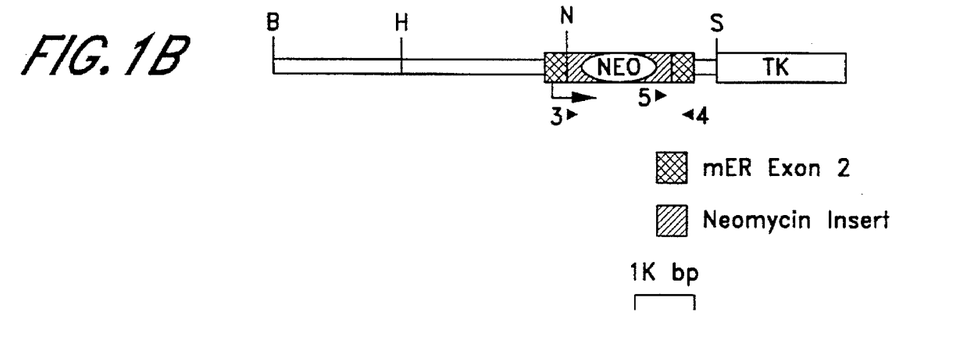

Gene targeting. To make the targeting construct for interrupting the reading frame of the mouse estrogen receptor on chromosome 10 (Sluyser et al., *J. Steroid Biochem.* 31: 757–761 (1988)), exon 2 of the ER gene was isolated in a 10 kb Bam HI genomic DNA fragment (FIG. 1A and B). Exon 2 contains the start codon and the N-terminal domain of the ER. The neomycin resistance gene was cloned into a Not I site in this domain to disrupt the ER reading frame. The HSVtk gene was added to increase the efficiency of finding targeted mouse ES cells.

Figure 1C:
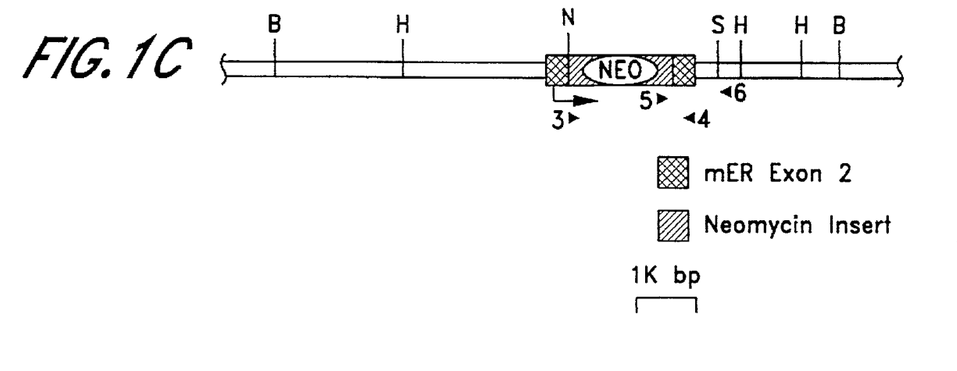

Electroporation was used to introduce the targeting construct into ES cells which were then exposed to G418 and ganciclovir. About 1800 surviving colonies were screened with primers 5 and 6 to find two in which homologous recombination had occurred as evaluated by the amplification of a 649 bp fragment diagnostic of targeting (FIG. 1C). Southern blot analysis with a neomycin probe confirmed that the targeted construct was integrated at a single site.

Generating animals. Cells from one of these targeted ES clones were injected into blastocysts, and four male and four female chimeras were obtained. After several matings with different males the chimeric females showed no germ line transmission. Two chimeric males transmitted the targeted gene through their germ line to produce heterozygous male and female animals. Heterozygous animals were then mated to produce homozygous animals. Primers 3 and 4, which bracket the neomycin integration site in the ER gene, allow detection of the presence of the wild type ER gene. PCR amplification was used to distinguish homozygous mutants (giving a 649 bp band only) from heterozygotes (giving a 649 bp and a 239 bp band) and from normal animals (giving only a 239 bp band). PCR products were further characterized by restriction enzymes where the non-targeted band (239 bp) was cut by Not I producing two bands of expected size 43 and 186 bp. The targeted mutant ER product of 649 bp did not cut; subsequent DNA sequencing showed that the targeted product contained the expected nucleotide sequence.

Breeding data. A total of 48 heterozygous matings were performed generating 361 offspring with a normal average litter size of 8 pups. The genotype frequencies are show in Table 1. There was no apparent gender preference, since almost equal numbers of male and female progeny were produced throughout all three genotype groups. Relative birth frequency of homozygous mutant animals was slightly lower than expected for a Mendelian distribution and was less than that found in the wild type group. However, statistical analysis using a Chi square goodness of fit test indicated that the deviation from expectation was not significant.

TABLE 1

Frequency of Pup Genotypes from Heterozygous Matings

|  | W | WM | M | TOTAL |
| --- | --- | --- | --- | --- |
| MALES | 56 (15) | 95 (26) | 31 (9) | 182 (50) |
| FEMALES | 54 (15) | 86 (24) | 39 (11) | 179 (50) |
| TOTAL | 99 (30) | 181 (50) | 70 (20) | 361 (100) |

Numbers of offspring from a total of 48 heterozygous matings are reported for each group, wild type (W), heterozygote (WM), and homozygous mutant (M). Numbers in parentheses represent the percent of offspring in each group. Chi square goodness of fit test of deviation from Mendelian ratio was not significant at P=0.07.

Phenotype of the animals. The external phenotypes of animals of both sexes that were homozygous for the disrupted gene were normal. Internally at a gross level only the females differed from normal. Sexual development was female, but the uteri were hypoplastic and the ovaries lacked detectable corpus lutea.

Histologically, the uteri appeared abnormal and hyperemic cystic ovaries were apparent. A histological section of an ovary from a wild type animal revealed follicles and corpus lutea. In contrast, ovaries from the homozygous mutant animals showed classic cystic and hemorrhagic follicles containing few if any granulosa cells. A few primary follicles could be seen, but no corpus lutea were observed in any of these ovaries. The histology of the uterus showed the presence of all major uterine cell types, but the stromal, epithelial and myometrial tissue compartments were present in diminished size. Uterine glands were present as well as ciliated epithelial cells in the oviduct.

Males appeared overtly normal, but testis weight was low compared to wild type or heterozygote animals. On the other hand, seminal vesicle and coagulating gland weights were not significantly different. Sperm were present in the testis and epididymus, however the sperm count was low at only 10% the control level.

Responses to estrogen. To test for estrogen responsiveness, adult females were treated for three days with estradiol at levels known to increase uterine wet weight, produce hyperemia and alter vaginal epithelial cytology in normal animals (Turner, C. D., General Endocrinology (W. B. Saunders, New York, 1965). The wild type and heterozygous animals responded normally compared to the untreated control by an increase in uterine wet weight of 3–4 fold. The uteri from wild type and heterozygotes became hyperemic after a three day bioassay. However, the homozygous ER disrupted animals did not respond with either an increase in uterine weight or hyperemia. Unlike wild type and heterozygous animals, treatment of ER disrupted animals with estradiol for 4–6 hours showed no uterine water imbibition or uterine hyperemia. Vaginal histology after estradiol treatment showed an increase in number of cornified epithelial cells in the wild type and heterozygous animals, but was unaltered in ER disrupted animals.

Estrogen binding. Ligand binding analyses of uterine tissue from the ER disrupted animals showed detectable estradiol binding (Korach, K. S., Endocrinology 104: 1324–1332 (1979)) at about 5% of the wild type level (60–70 fm/100 µg DNA) with a binding dissociation constant similar to that of the wild type (0.7 nM). Low concentrations of ER protein were confirmed by an Elisa assay (Abbott Laboratories, North Chicago, Ill.) using two antibodies to the C-terminal end of the ER protein. "Splicing over" of insertional mutations (Luetteke et al., Cell 73: 263–278 (1993)) or nonsense codons (Dietz et al., Science 259: 680–683 (1993)) has been observed previously. In vivo reinitiation of translation after a nonsense mutation, resulting in a ligand nonresponsive receptor protein, has also been seen previously in the steroid receptor superfamily (Gaspar et al., Proc. Nat. Acad. Sci. USA 88: 8606–8610 (1991)). An altered form of the normal receptor may be synthesized after the ER gene disruption. If so, it is incapable of mediating estrogen responsiveness, either because of its structure or because it is synthesized at too low a level. It has been shown that uterine responsiveness to estrogen does not occur if receptor levels are decreased to below 20% of control (Gibson et al., Endocrinology 129: 2000–2010 (1991)).

Fertility. All homozygous mutant females were infertile. None showed any lordosis posture or receptiveness to wild type males even when challenged with estrogen treatment. This behavior suggests absence of estrogen responsiveness in the central nervous system. Male fertility was tested with harem pairings to known fertile wild type females. Fertility was reduced, but not abolished, as only 3 of 15 males producing any offspring. However, the males that initially demonstrated fertility have not to date sired any more litters after several pairings. No plugs were found in any of the matings of both sexes of homozygous mutant animals, with the exception of the 3 fertile males.

While particular embodiments of the invention have been described in detail, it will be apparent to those skilled in the art that these embodiments are exemplary rather than limiting, and the true scope of the invention is that defined within the attached claims.

What is claimed is:

1. A mouse homozygous for a targeted disruption in exon-encoding DNA of the estrogen receptor gene, wherein said targeted disruption inhibits production of wild type estrogen receptors so that the phenotype of a female homozygous for said targeted disruption is characterized by a lack of estrogen responsiveness, and wherein said targeted disruption is produced by homologous recombination in murine embryonic stem cells.

2. A mouse heterozygous for a targeted disruption in exon-encoding DNA of the estrogen receptor gene, wherein said targeted disruption inhibits production of wild type estrogen receptors so that the phenotype of a female homozygous for said targeted disruption is characterized by a lack of estrogen responsiveness, and wherein said targeted disruption is produced by homologous recombination in murine embryonic stem cells.

3. A chimeric mouse some of whose germ cells contain a targeted disruption in exon-encoding DNA of the estrogen receptor gene, wherein said targeted disruption inhibits production of wild type estrogen receptors so that the phenotype of a female homozygous for said targeted disruption is characterized by a lack of estrogen responsiveness, and wherein said targeted disruption is produced by homologous recombination in murine embryonic stem cells.

4. A murine embryonic stem cell containing a targeted disruption in exon-encoding DNA of the estrogen receptor gene, wherein said targeted disruption inhibits production of wild type estrogen receptors so that the phenotype of a female mouse homozygous for said targeted disruption is characterized by a lack of estrogen responsiveness, and wherein said targeted disruption is produced by homologous recombination.

5. A blastocyst containing the embryonic stem cell of claim 4 containing said targeted disruption.

6. A cell of the mouse of claim 1 containing said targeted disruption.

7. The mouse of claim 1, wherein said targeted disruption is targeted to the estrogen receptor gene by homologous recombination with a DNA construct comprising exon-encoding DNA of the mouse estrogen receptor gene and an insertional disruption contained therein.

8. The mouse of claim 7, wherein said exon is exon 2.

9. The mouse of claim 7, wherein said insertional disruption is neomycin resistance gene as a positive selectable marker gene.

10. A method of producing a mouse homozygous for a targeted disruption in exon-encoding DNA of the estrogen receptor gene, wherein said targeted disruption inhibits production of wild type estrogen receptors so that the phenotype of a female homozygous for said targeted disruption is characterized by a lack of estrogen responsiveness, comprising the steps of:

(a) implanting into an embryo of an ancestor of said mouse a murine embryonic stem cell containing said targeted disruption produced by homologous recombination;

(b) allowing said embryo to develop to term to produce a chimeric mouse;

(c) breeding said chimeric mouse, wherein said chimeric mouse is capable of transmitting said targeted disruption, to produce a heterozygous mouse; and (d) breeding said heterozygous mouse to produce said homozygous mouse.

11. A method of producing a mouse heterozygous for a targeted disruption in exon-encoding DNA of the estrogen receptor gene, wherein said targeted disruption inhibits production of wild type estrogen receptors so that the phenotype of a female homozygous for said targeted disruption is characterized by a lack of estrogen responsiveness, comprising the steps of:

(a) implanting into an embryo of an ancestor of said mouse a murine embryonic stem cell containing said targeted disruption produced by homologous recombination;

(b) allowing said embryo to develop to term to produce a chimeric mouse; and (c) breeding said chimeric mouse, wherein said chimeric mouse is capable of transmitting said targeted disruption, to produce said heterozygous mouse.

12. A method of producing a chimeric mouse some of whose germ cells contain a targeted disruption in exon-encoding DNA of the estrogen receptor gene, wherein said targeted disruption inhibits production of wild type estrogen receptors so that the phenotype of a female homozygous for said targeted disruption is characterized by a lack of estrogen responsiveness, comprising the steps of:

(a) implanting into an embryo of said mouse a murine embryonic stem cell containing said targeted disruption produced by homologous recombination; and (b) allowing said embryo to develop to term to produce said chimeric mouse.

13. The method of claim 10, wherein said targeted disruption is targeted to the estrogen receptor gene by homologous recombination with a DNA construct comprising exon-encoding DNA of the mouse estrogen receptor gene and an insertional disruption contained therein.

14. The method of claim 13, wherein said exon is exon 2.

15. The method of claim 13, wherein said insertional disruption is neomycin resistance gene as a positive selectable marker gene.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:1:

CGCTGCTGAG CCCTCTGCGT G     21

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

GTTGAACTCG TAGGCGGCGC CCTC     24

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:3:

CGGTCTACGG CCAGTCGGGC ACC     23

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GTAGAAGGCG GGAGGGCCGG TGTC 24

( 2 ) INFORMATION FOR SEQ ID NO:5:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TTCCACATAC ACTTCATTCT CA 22

( 2 ) INFORMATION FOR SEQ ID NO:6:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

CTCCACTGGC CTCAAACACC TG 22